United States Patent [19]

Boretos

[11] 4,254,774
[45] Mar. 10, 1981

[54] BALLOON CATHETER AND TECHNIQUE FOR THE MANUFACTURE THEREOF

[75] Inventor: John W. Boretos, Rockville, Md.

[73] Assignee: The United States of America as represented by the Department of Health, Education and Welfare, Washington, D.C.

[21] Appl. No.: 12,222

[22] Filed: Feb. 14, 1979

[51] Int. Cl.³ .......................................... A61M 25/00
[52] U.S. Cl. .................................... 128/348; 128/262; 128/344; 128/349 B
[58] Field of Search ............... 128/262, 344, 246, 129, 128/325, 348–351, 756, 658

[56] References Cited

U.S. PATENT DOCUMENTS

| | | | |
|---|---|---|---|
| 3,050,066 | 8/1962 | Koehn | 128/325 X |
| 3,664,328 | 5/1972 | Moyle et al. | 128/756 |
| 3,911,927 | 10/1975 | Rich et al. | 128/349 R |
| 4,029,104 | 6/1977 | Kerber | 128/348 |
| 4,085,757 | 4/1978 | Pevsner | 128/325 |
| 4,109,659 | 8/1978 | Sheridan | 128/349 R |

FOREIGN PATENT DOCUMENTS 454642  7/1928  Fed. Rep. of Germany ........... 128/262

OTHER PUBLICATIONS

Kerber–"Diagnostic Radiology", Sep. 1976, Univer. Oregon.
Serbinenko–"J. Neurosurgery", vol. 41, Aug. 74, pp. 125–145.

Primary Examiner—Dalton L. Truluck
Attorney, Agent, or Firm—Browdy and Neimark

[57] ABSTRACT

A single-lumen, one piece catheter approximately 0.04 inch in diameter with an integral balloon at its end having a wall thickness of 0.005 inch or less, sufficiently small to be retractible by suction into the catheter and to be extensible at a desired site by fluid pressure. The balloon may have a calibrated restricted leak aperture. The balloon portion of the catheter is made by heating a portion of the catheter tubing, stretching the tubing lengthwise, and applying fluid pressure to the tubing. The apparatus for forming the balloon includes a spring-loaded clamp to hold the tubing at one end, a capstan to hold the tubing at the other end, a heating coil wrapped around the tubing near the clamped end thereof and mounted with the clamp, and a mechanism for controlling the pressure and volume of the pressurizing gas entering the lumen of the tube in accordance with the retractile movement of the spring-loaded clamp.

6 Claims, 5 Drawing Figures

U.S. Patent      Mar. 10, 1981      4,254,774
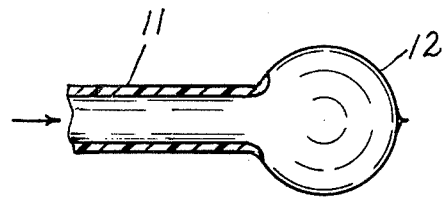
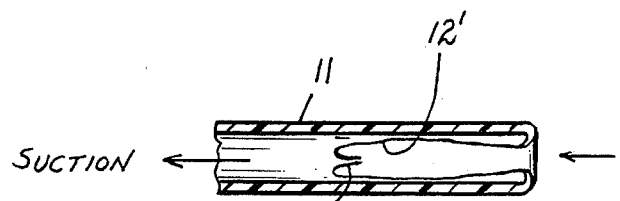
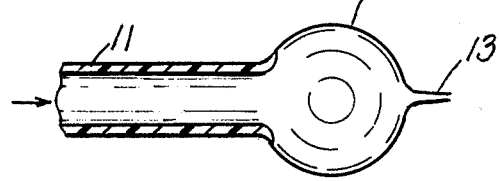
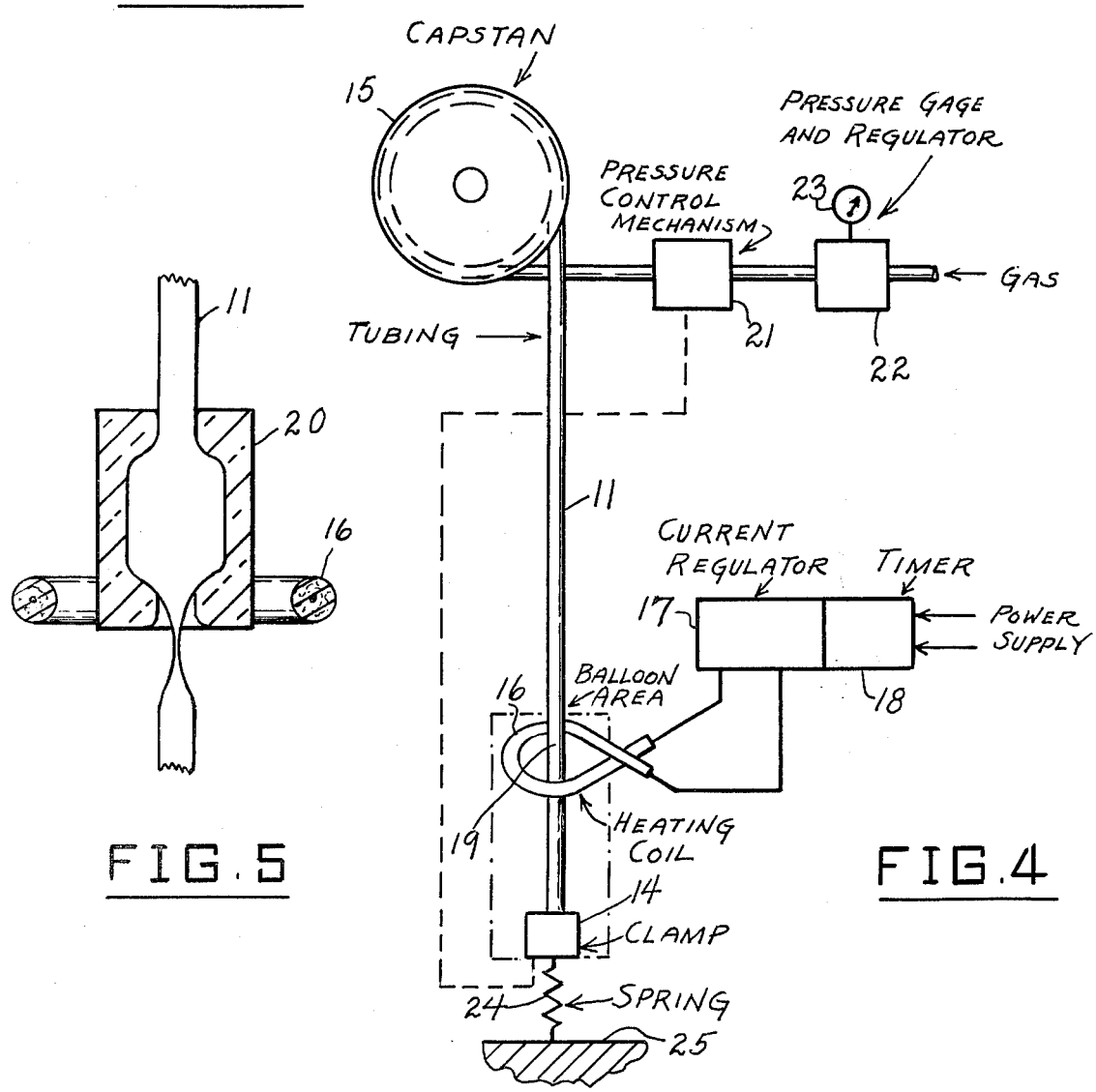

BALLOON CATHETER AND TECHNIQUE FOR THE MANUFACTURE THEREOF

FIELD OF THE INVENTION

This invention relates to balloon catheters, and more particularly to a balloon catheter wherein the balloon is a continuous, non-interrupted integral part of the catheter wall, free of seams or joints.

BACKGROUND OF THE INVENTION

Balloon catheters are useful tools of the clinical radiologist and surgeon and find application in diagnosing and treating innumerable ailments throughout the body. They have been used in virtually all passageways from blood vessels, urinary tracts, or the like, to nasal and throat openings. They function to block flow of blood, air, urine, etc., to scrape vessel walls for the removal of clots, to block the flow of escaping air, and for numerous other uses. Generally, these devices consist of plastic or rubber tubing to which a rubber sleeve is mechanically fastened to simulate a balloon. These fastenings usually consist of several wraps of fiber to anchor the edges of the balloon, followed by an overcoat of rubber or plastic. As the sizes become smaller and the tubing becomes softer, these balloons are more difficult to construct and suffer from a lack of strength and reliability. Consequently, they have not been available for use in diagnosis and treatment in many situations. Thus, there is a significant need for very small-diameter catheters which exhibit a high degree of flexibility and reliability and, because of their gossamer nature, are capable of navigating the tortuous paths of small (less than 1 mm) lumen vessels leading to tumors, arteriovenous malformations, aneurysms, angiomas, parathyroid adenomas, and the like.

Existing balloon catheters have various serious shortcomings, mainly because the balloon is connected to the cathetic tubing wall by seams or joints which present difficult fabrication problems, which are subject to leakage or rupture, and which interfere with the smooth movement of the catheter in its intended passage because the seams or joints are relatively bulky.

A preliminary search of the prior art reveals the following prior U.S. Pat. Nos. of interest:
Koehn,—3,050,066
Dereniuk,—3,528,869
Vasquez et al,—3,833,004
Dyke,—4,003,382
Kerber,—4,029,104

SUMMARY OF THE INVENTION

The device of the present invention overcomes the shortcomings of existing balloon catheters by providing the balloon as an integral and unitary part of the wall of the cathetic tubing, free of seams or joints that might be subject to leakage or rupture. Also, the device of the present invention is of a nature to allow a wide variety of materials to be used for catheters, namely, it allows the use of any thermoplastic or thermosensitive material. This feature of versatility, according to the present invention, opens up new applications for catheters, for instance, it allows the catheter to be specially treated for antithrombogenicity, antisepsis, or the like, by surface modification and other chemical treatments or alterations. According to the present invention, balloon catheters can be made as small as several mils in diameter with precision and reliability. They can be either constructed with (1) a terminal balloon and no open lumen at its end, (2) a terminal balloon with a calibrated and controllable leak at its end, or (3) any number or combination of the above two types.

A balloon without a terminal lumen can be readily constructed using the technique of the present invention. Temporary or permanent blocking of vessels of any size can be realized with these catheters. Temporary blocking, for example, is especially useful for (a) clinical and electro-physiological study of the collateral blood supply of a vascular system distal to an occluded vessel, (b) angiographic investigation of the collateral blood flow from systems adjacent to that of the occluding vessel, (c) trials of the therapeutic effect of occluding a vessel functioning as a shunt or the afferent vessel of an arteriovenous aneurysm, and (d) study of the effect of reducing or eliminating blood flow in a vessel.

The use of a balloon with a calibrated leak, in accordance with the present invention, in very small (less than 1 mm diameter) vessels could provide for (a) selective angiography of a vessel located either distal or proximal to an occluded section of a vessel, (b) injection of fluid-hardening polymers into an aneurysm, blocking a malformation or isolating a tumor, (c) injection of radiopaque materials for tumor staining for disclosure, and (d) supplying chemotherapeutic agents locally, as to a tumor. A calibrated leak can be built into the terminal end of the balloon catheter during fabrication, as will be presently described, prior to expanding the wall to form the balloon. With this design, the balloon will inflate under predetermined pressure before "leaking" pressure or fluid. Varying degrees of inflation can serve two functions: (1) to block the vessel and prevent retrograde flow, or (2) partially inflated, to act as a float to carry the catheter to otherwise inaccessible areas, utilizing the flow of blood around and against it to propel it along. The combination of its small size, gossamer nature, and reliably inflatable balloon, provided by the technique of the present invention, allows the catheter to traverse through small and winding passages leading to the brain, liver, pancreas, spleen, kidneys, etc. Once the catheter has arrived at the intended site, additional pressure will allow whatever fluid or agent which is to be delivered to "leak-out" of the lumen. The amount delivered is a function of the applied pressure, the size of the capillary, the elapsed time, and the viscosity of the supplied substance.

The catheter of the present invention relies on complete flexibility to perform its function, namely, of traversing 1 mm and smaller vessels while being free to flex over small radii of less than one-half of the vessel diameter so that it can readily enter smaller branch vessels located at acute angles. For this reason, even the softest of catheter materials must possess extremely thin walls (i.e., less than 0.005 inch, and preferably 0.002 inch or less) and no seams or joints that might add stiffness and subsequent resistance to movement such as in the previously employed devices.

The catheter of the present invention has a one-piece, i.e. unitary, construction which minimizes the possibility of detachment or separation of portions thereof accidentally in a critical area of the body where harm may be incurred to the patient, such as in the area of the brain or lungs. In these small sizes, bond lines, cement joints, or fasteners employed with previously used catheter devices must be concomitantly small and weaker than on conventional size catheters. Furthermore, as the inner bore of catheters becomes increasingly smaller, greater pressures must be exerted along the catheter to deliver a drug or medication through it. These higher pressures could also add to the risk of destruction or accidental rupture of catheters of the "assembled" type, whereas all of these problems are avoided by the simple one-piece construction of a catheter according to the present invention. Also, the device of the present invention is well suited for automation in its fabrication, without requiring complicated and expensive assembly equipment such as is required in fabricating previously employed catheters.

Accordingly, a main object of the invention is to provide a balloon catheter which overcomes the deficiencies and shortcomings of the previously employed balloon catheters.

A further object of the invention is to provide an improved balloon catheter which is of continuous, non-interrupted, one-piece construction, free of seams or joints.

A still further object of the invention is to provide an improved balloon catheter which has an integral balloon of very small wall thickness so that the balloon may be readily retracted into the associated catheter tube to facilitate the insertion and placement of the catheter, and so that the balloon may be readily inflated at its intended site.

A still further object of the invention is to provide an improved balloon catheter of continuous smooth, one-piece construction which has a balloon of very small wall thickness and which is easy and inexpensive to manufacture, which is reliable in operation, which is capable of varying degrees of inflation, and which can be efficiently used for navigating the tortuous paths of relatively small-lumen vessels.

A still further object of the invention is to provide an improved technique and apparatus for fabricating balloon catheters, allowing the use of a wide range of thermoplastic or thermosensitive materials and requiring relatively simple and inexpensive fabrication equipment.

A still further object of the invention is to provide an improved completely flexible balloon catheter which includes an integral balloon of very small wall thickness and which is provided with a calibrated leak orifice for enabling a substantial range of functions, such as selective angiography of a vessel located either proximal or distal to an occluded section of the vessel, injection of desired material for blocking or isolating a tumor, injection of radiopaque materials for tumor staining, or the like, supplying chemotherapeutic agents locally, or for other desired purposes.

A still further object of the invention is to provide an improved balloon catheter which has a smooth uninterrupted external contour and has complete flexibility for accomplishing its function, namely, which is capable of traversing 1 mm and smaller vessels while being free to flex over small radii of less than one-half of the vessel diameter so that it can readily enter smaller branch vessels located at acute angles, the construction being such as to provide safety from accidental disintegration or separation into segments or pieces in critical areas of the body where harm may be incurred to a patient, such as in the area of the brain or lungs.

A still further object of the invention is to provide a novel and improved safe and reliable design for a balloon catheter which offers a greater choice than was previously available of materials from which the balloon catheter may be constructed, and which allows miniaturization to an extent heretofore unobtainable to occlude small vessels, and which allows passage of various liquids through the catheter under controlled conditions, the improved balloon catheter being readily fabricated from conventional materials, and wherein its manufacture readily lends itself to large scale production methods.

BRIEF DESCRIPTION OF THE DRAWINGS

Further objects and advantages of the invention will become apparent from the following description and claims, and from the accompanying drawings, wherein:

FIG. 1 is an enlarged longitudinal cross-sectional view of the inflated balloon and adjacent tube portion of a balloon catheter constructed in accordance with the present invention.

FIG. 2 is a longitudinal cross-sectional view similar to FIG. 1 but showing a balloon catheter with a calibrated leak orifice according to the present invention.

FIG. 3 is a longitudinal cross-sectional view of the structure of FIG. 2, with the balloon element retracted into the catheter tube by suction.

FIG. 4 is a diagrammatic illustration of a typical apparatus for fabricating a balloon catheter employing the fabrication technique of the present invention.

FIG. 5 is an enlarged fragmentary vertical cross-sectional view showing the use of a contoured sleeve or mould employed for shaping a balloon, with the apparatus of FIG. 4.

DESCRIPTION OF PREFERRED EMBODIMENTS

Referring to the drawings, in FIG. 1 a catheter tube 11 is provided with an integral terminal balloon 12 in accordance with the present invention, shown in inflated condition. The catheter tube may comprise any suitable thermoplastic or thermosensitive material that can be made in the form of tubing, for example, polyurethanes, copolyester polymers, thermoplastic rubbers, silicone-polycarbonate copolymers, polyethylene ethyl-vinyl-acetate, or combinations of these and/or others. Tubing of a predetermined wall thickness-to-diameter relationship is selected so that when the balloon 12 is produced it results in a durable yet compliant membrane. This could range from 1 mil to 20 mils wall thickness of the balloon, depending upon the overall diameter of the tubing and the size of the balloon desired. Also, the thickness of the balloon membrane can be regulated. For example, a 40 mil diameter tube 11 with a 2 mil wall thickness could readily produce a 100 mil diameter balloon, or a 5 mil tube could produce such a 100 mil diameter balloon, except that the balloon membrane would be thinner. Therefore one can tailor the characteristics of the balloon to suit a particular application. Length, diameter and shape of the balloon can also be regulated.

In one embodiment, for example, for a 40 mil diameter tube 11, the wall thickness of the balloon is 5 mils or less. A balloon wall thickness of 2 mils has been employed with success. As it is desirable, as noted above, for the catheter to traverse vessels of 1 mm (i.e. 0.03937" or 39.37 mils), it follows that the diameter of the tube 11 for such uses must be somewhat less than this dimension.

As was previously mentioned herein, a balloon catheter such as is shown in FIG. 1 can be employed for temporarily or permanently blocking vessels of any size. More specifically, as also mentioned above, temporary blocking finds special utility in achieving the following purposes: (1) the clinical and electrophysiological study of the collateral blood supply of a vascular system distal to an occluded vessel, (2) the angiographic investigation of the collateral blood flow from systems adjacent to that of an occluded vessel, (3) trials of the therapeutic effect of occluding a vessel functioning as a shunt, or the afferent vessel of an arteriovenous aneurysm, and (4) the study of effects accruing from the reduction or elimination of blood flow in a vessel.

It will be seen from FIG. 1 that the balloon 12 is an integral part of the wall of the cathetic tubing and is free of seams or joints that might be subject to leakage or rupture.

FIG. 2 illustrates a balloon catheter similar to FIG. 1 but with a calibrated leak nozzle 13 formed as a terminal lumen for the balloon, designated at 12'.

The thin-walled balloon 12 or 12' may be retracted into the catheter tubing 11, as shown in FIG. 3, by applying light suction to the tube, using a syringe or other suitable suction means connected to the distal end of the catheter tubing 11, whereupon the balloon immediately and completely retracts. This results in a "disappearing" balloon with a straight smooth-walled catheter. This can be moved along unobstructedly until it reaches a point further within a vascular network, for example, where it then becomes advantageous to deploy the balloon (by applying positive fluid pressure to the catheter) and allow the flow of blood to take over and push against the balloon for forward movement (i.e., propulsion). Once the catheter has performed its function (as previously described) the balloon is readily retracted into the lumen proper of the tube 11 by applying slight suction to the exterior distal end of the catheter tube. Even though the small leak nozzle (of the modification of FIG. 2) exists at the balloon end, it does not interfere with the retraction, and the balloon readily collapses. The invaginated balloon is then out of the way and allows for smooth withdrawal of the catheter.

To form the balloon, the catheter tubing is heated locally, i.e., in the area where the balloon is desired, until the tubing is soft and/or semi-molten. The exact temperature of the plastic and the amount of heat required to be applied will vary, depending upon the softening temperature of the material being used, but will usually be within the 100°–250° C. range. At this stage the tubing 11 is stretched lengthwise, causing the heated portion to greatly narrow to form a constriction. Any size restriction can be obtained by regulating the amount of heat applied, the speed of application, the time, and the length of pulling. Openings of capillary size (or total closure) may be achieved. Excess tubing is cut off at the constriction upon completion of the pulling step, and/or coincident with the cutting the heat is removed and the balloon 12 or 12' is formed by applying a predetermined amount of gas pressure to the inner lumen of the tubing. This pressure causes a circumferential expansion of the area which has been heated selectively. Most thermoplastic or thermosensitive materials will lose their heat in a matter of seconds and will "set" permanently into this inflated configuration. More rapid cooling can be provided by passing air, mist or water over the previously heated surfaces. The size and shape of a plain spherical balloon is regulated by the amount of heat applied, the length of the area that receives the heat, and the pressure and/or volume of the gas applied. Unusual sizes and shapes can be obtained, if desired, by providing an internally contoured sleeve 20, defining the desired size and shape, of glass, metal or similar heat dissipating substance around the balloon to serve as a mould, as shown in FIG. 5.

The balloon 12, without the terminal lumen element 13, is made in the same fashion as the balloon 12', except that the heating time and temperature to form the capillary are extended to a point where a permanent welding or fusing of the end of the balloon-defining thinned wall area occurs, closing off said end.

FIG. 4 diagrammatically illustrates a typically apparatus for performing the above-described method. The tubing 11 is held in the apparatus by a spring-loaded clamp 14 at one end and is supportingly wound on a capstan spool or pulley 15 at the other end. The capstan spool or pulley 15 serves to immobilize the tubing 11 without undue strain on collapse of the tubing lumen. A heating coil 16, including resistance wire, such as nichrome wire, surrounds the tubing 11 near its clamped end. A current regulating device of conventional design, shown at 17, and a timer 18 control the amount of energy imparted to the coil 16. In response to localized heating of the tubing by the coil 16, the spring-loaded clamp 14 elongates the tubing locally to narrow its lumen, and at the same time the heated coil radiates heat to the area 19 above the narrowed lumen portion which will subsequently become the balloon. The clamp 14 and coil 16 are mounted together and move as one assembly.

The clamp 14 is suitably coupled to a conventional pressure control mechanism 21 connected to the tubing 11 at the far end thereof, allowing pressure-controlled gas to enter the lumen of the tubing. The conventional pressure control mechanism 21 can be of a type comprising a solenoid-actuated drive for a syringe or other piston-actuated device. Gas pressure and volume may be further controlled by a conventional regulator 22 having a pressure gage 23. The spring loading of the clamp 14 may be provided by a suitable spring 24 resiliently connecting clamp 14 to an adjacent stationary anchoring member, shown at 25.

While certain specific embodiments of improved balloon catheters and a method and apparatus for forming same have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A device for passage into a body vessel or passageway of diameter 1 mm or smaller comprising a unitary, integral and seamless balloon catheter of smooth uninterrupted contour having a single-lumen, flexible elongated catheter tube of diameter less than 40 mils integrally formed at one end with means to occlude the body vessel or passageway and comprising an inflatable balloon of one piece construction with said catheter tube having a wall thickness of less than 5 mils and sufficiently small relative to that of said tube to allow said balloon to be retracted by suction into said tube.

2. The balloon catheter of claim 1, and wherein said one-piece tube and balloon comprises thermoplastic material.

3. The balloon catheter of claim 2, and wherein said balloon has a wall thickness of approximately 0.002 inch.

4. The balloon catheter of claim 1, and wherein said balloon is provided with means for passage therefrom of a fluid into the body vessel or passageway, said means comprising a restricted leak aperture at the leading end of the balloon.

5. The balloon catheter of claim 4, and wherein said restricted leak aperture is in the form of a nozzle element unitary with the end of the balloon.

6. A balloon catheter of claim 5, said balloon having a wall thickness of approximately 2 mils.

* * * * *